United States Patent
Lucka et al.

(10) Patent No.: US 8,084,409 B2
(45) Date of Patent: Dec. 27, 2011

(54) MICRODERMABRASION SOAP BAR COMPOSITIONS AND METHODS OF PREPARING SAME

(75) Inventors: Lynn Lucka, New York, NY (US); Patricia A. Mullen, Columbia, TN (US)

(73) Assignee: Bella Bella, Inc., New York, NY (US)

( * ) Notice: Subject to any disclaimer, the term of this patent is extended or adjusted under 35 U.S.C. 154(b) by 100 days.

(21) Appl. No.: 12/427,683

(22) Filed: Apr. 21, 2009

(65) Prior Publication Data

US 2010/0267599 A1    Oct. 21, 2010

(51) Int. Cl.
*A61K 7/50* (2006.01)

(52) U.S. Cl. ........ 510/141; 510/139; 510/152; 510/447; 424/401

(58) Field of Classification Search .......................... None
See application file for complete search history.

(56) References Cited

U.S. PATENT DOCUMENTS

| | | |
|---|---|---|
| 4,957,747 A | 9/1990 | Stiefel |
| 4,992,476 A | 2/1991 | Geria |
| 5,753,245 A | 5/1998 | Fowler et al. |
| 5,910,476 A | 6/1999 | Kinsman et al. |
| 6,290,976 B1 | 9/2001 | Messenger |
| 7,025,976 B2 | 4/2006 | Fox et al. |
| 7,179,152 B1 | 2/2007 | Rhoades |
| 7,179,477 B2 | 2/2007 | Gupta |
| 7,417,015 B2 | 8/2008 | Volz et al. |
| 2004/0096260 A1 | 5/2004 | Rhoades |
| 2005/0037038 A1 | 2/2005 | Gupta |
| 2007/0025949 A1 | 2/2007 | Hansenne et al. |
| 2007/0161527 A1 | 7/2007 | Mercurio et al. |

*Primary Examiner* — Necholus Ogden, Jr.
(74) *Attorney, Agent, or Firm* — Ward & Zinna, LLC

(57) ABSTRACT

A light-colored soap bar composition for at-home microdermabrasion comprising from approximately 8% to approximately 15% by weight of an abrasive comprising magnesium oxide, having a mean particle size diameter from approximately 120 to approximately 200 micrometers, and from approximately 0.5% to approximately 3.5% total dispersing agents by weight, which help to disperse the abrasives uniformly within the soap bar. The dispersing agents comprise oil and butter components which help to uniformly incorporate the abrasives into the soap bar composition without having to significantly alter the foamability and integrity of the soap bar.

22 Claims, No Drawings

MICRODERMABRASION SOAP BAR COMPOSITIONS AND METHODS OF PREPARING SAME

FIELD OF INVENTION

The present invention relates generally to microdermabrasion soap compositions and methods of preparing same, and particularly to an improved skin cleansing soap bar composition comprising dispersing agents and a high concentration of uniformly dispersed abrasive including magnesium oxide having a large mean particle size.

BACKGROUND OF THE INVENTION

In humans, the skin cell turnover cycle begins at the basal layer of the dermis, where new skin cells are generated. The dermis is the mid-layer of the skin which contains blood vessels, nerves, hair roots and sweat glands. The new skin cells produced by the basal layer gradually migrate upwards, toward the outer layer of the skin, the epidermis. During this migration, the cells lose their central nucleus, alter their form, and start to produce keratin that causes them to harden. Consequently, the top layer of the epidermis, the stratus corneum, comprises such keratinized skin cells that take the form of flattened discs. These flattened cells, now called corneocytes, are effectively dead and slough off about every two to four weeks. The stratum corneum acts as the body's defense against external stimuli, water, and pathogens.

However, an excess accumulation of corneocytes is a common problem that is caused by various factors such as hormonal imbalance, age, or skin disorder. Such build up of corneocytes gives a rough and dull appearance to the skin and can also lead to skin ailments such as psoriasis, Keratosis Pilaris, folliculitis, acne, comedones, and milia. The conditions are exacerbated when oil and dirt are present due to insufficient or inefficient cleansing.

Regular exfoliation procedures have been used for centuries to supplement the natural skin cell turnover cycle. Exfoliation is a process of removing dead skin cells, such as corneocytes, oil, and dirt from the skin, and can be achieved through mechanical or chemical means. The chemical methods are called chemoexfoliation or "chemical peel" and commonly utilize alpha-, beta-, or polyhydroxy acids. The acids are applied to the skin in high concentrations by a dermatologist, or in lower concentrations by the person using over-the-counter products. The chemical peel produces a controlled partial injury to the skin by stripping off superficial skin layers. During the ensuing healing period, the epidermis is regenerated, and in case of a deeper chemical peel, the restructuring of the new dermal connective tissue takes place. This results in an improved clinical appearance of the skin. However, the drawbacks of chemoexfoliation such as cost, pain, and a long recovery period, deter many people from choosing this procedure.

Another type of exfoliation is a mechanical exfoliation of the skin using abrasives. This process involves physically scrubbing the skin with an abrasive. Traditional abrasives include crushed apricot kernel, almond shells, sugar or salt crystals, pumice, and loofahs. Co-applicant, Lynn Lucka, has previously been issued a patent on exfoliating compositions incorporating corundum ($Al_2O_3$) particles (See U.S. Pat. No. 6,290,976).

Dermabrasion is one type of such mechanical procedure which involves aggressively abrading the surface of the skin with a wire brush or a diamond wheel. The procedure minimizes the appearance of scars, dark spots, sun damages, and wrinkles. Despite its effectiveness, the associated pain requires local anesthetic and/or sedation that must be administered by a qualified physician. There is also an extensive post-procedure recovery period that lasts for a number of months due to the deep injury to the skin. Moreover, side effects of dermabrasion such as localized hyperpigmentation or hypopigmentation, infection, or hypersensitivity of the skin sometimes outweigh the benefits of the procedure.

Thus, a less invasive procedure called microdermabrasion or particle skin resurfacing has gained an increasing popularity to treat conditions such as minor sun damage, fine lines and wrinkles, enlarged pores, and coarse textured skin. In a clinical setting, the microdermabrasion procedure typically involves a device that sprays microcrystals of abrasives across the skin's surface. The procedure is virtually painless and requires little or no recovery time. Combined with thorough cleansing, microdermabrasion can be an effective method of maintaining a healthy skin. However, microdermabrasion in a clinical setting is costly and regular visits to the dermatologist are inconvenient for many consumers.

As a cheaper and convenient alternative to clinical microdermabrasion treatments, many consumers turn to personal care products such as creams, liquid cleanser, and cleansing soap bars. Microdermabrasion soap bars typically contain abrasives having a particle size diameter between 100 and 120 microns such as corundum and pumice. However, abrasives of this size are not always aggressive enough to cause the desired polishing effect on areas of the skin having thick layers of stratum corneum. This is especially true when the abrasives in a personal care product are used by an untrained consumer. One solution to the problems is to use large abrasives with a mean particle size diameter from approximately 120 to approximately 220 microns. Such large abrasives provide extra abrading power capable of removing more dirt and dead cells without unnecessary irritation. The large abrasives also provide more tactile perception that the skin is being exfoliated compared to their smaller counterparts.

For a microdermabrasion soap bar to be effective, it is imperative that the large abrasives are dispersed evenly within the soap bar. Otherwise, the soap bar may disintegrate prematurely during its use. Further, uneven distribution of abrasives in a soap bar creates areas of the soap bar with a large concentration of abrasives leaving other areas with a small concentration of abrasives. This is problematic, as the concentrated areas are extremely irritating against the skin, while the small concentration areas provide virtually no abrading effect.

Notwithstanding the foregoing, it is difficult to incorporate large abrasives within a soap bar at an amount higher than about 8%, while simultaneously preserving some of the most favored characteristics of a soap bar (e.g. appearance, cleansing ability, mildness to the skin, integrity and foamability). For example, it is possible to uniformly disperse large abrasives in a soap bar by using oils alone, such as olive oil or palm oil. However, this is done at the expense of foamability and integrity of the soap bar. A microdermabrasion soap bar containing high amounts of large abrasives with oils alone, disintegrate prematurely during the manufacturing process. The foamability and integrity of a soap bar are important from a marketing perspective, as they are a measure of product quality. Generally, high lathering soap bars with a rigid structure are capable of cleaning more effectively compared to the ones with inferior foamability and integrity. To this end, it has been unexpectedly discovered that the effects oils on the foamability and the integrity of the soap bars is ameliorated by an incorporation of butters. Furthermore, the right proportions of butters and oils in a microdermabrasion soap bar composition aid in uniformly dispersing large abrasives in the soap.

The appearance of a soap bar is another important characteristic, especially from a marketing perspective. Often, consumers choose products by their appealing appearance. A light soap color is more appealing to the consumers, as it indicates cleanliness. However, many soap products on the market that utilize natural abrasives are dark in color—a characteristic not desired in an at-home soap product. In addition, it has been found that incorporation of high amounts of various abrasives alters the color characteristics of the soap. In an effort to solve this problem, it has been unexpectedly found that using a large amount of magnesium oxide crystals in a soap does not darken the color of the soap. The soap containing such magnesium oxide particles appears white or very light blue. In contrast, using a large amount of aluminum oxide crystals or pumice has been found to blacken the appearance of the soap upon incorporation.

SUMMARY OF INVENTION

It is therefore an object of the invention to provide a light-colored, personal cleansing soap bar composition containing high amounts of uniformly dispersed abrasives having a mean particle size diameter from approximately 120 to approximately 200 microns.

It is yet another object of the invention to provide a method of incorporating from approximately 8% to approximately 15% large abrasives by weight into a soap bar with dispersing agents that do not significantly alter the foamability and integrity of the soap bar.

It is another object of the invention to provide a method of manufacturing a light colored, personal cleansing soap bar containing from approximately 8% to approximately 15% by weight of uniformly dispersed Magnesium oxide having a mean particle size diameter from approximately 120 to approximately 200 microns, preferably approximately 150 microns without significantly altering the foamability and the integrity of the soap bar.

It is yet another object of the invention to provide a light-colored mild personal cleansing soap bar utilizing dispersing agents to evenly disperse abrasives having a large particle size within the soap bar.

It is yet another object of the invention to provide a microdermabrasion personal cleansing soap bar utilizing abrasives having large particle size and dispersing agents.

The present invention relates to a soap composition for at-home microdermabrasion comprising from approximately 8% to approximately 15% by weight of abrasives having a mean particle size diameter from approximately 120 to approximately 200 micrometers ("microns") and from approximately 0.5% to approximately 3.5% total dispersing agents by weight, which helps to disperse the abrasives uniformly within the soap. The permissible water content in the composition of the present invention is up to approximately 15%, preferably up to approximately 10% by weight to ensure the integrity of the soap bar. The foamability of the soap is not compromised by the incorporation of large abrasives. The dispersing agents comprise an oil component and a butter component. The oil and butter components contain saturated or unsaturated aliphatic chains having about 8 to about 24 carbons. The dispersing agents may also comprise from approximately 1 to approximately 15% glycerin by weight and from approximately 0.1% to approximately 1.5% essential oils by weight. The dispersing agents help to uniformly incorporate abrasives into the soap composition without having to significantly alter the foamability of the soap.

DETAILED DESCRIPTION OF THE INVENTION

A detailed illustrative embodiment of the present invention is disclosed herein. However, the present invention may be embodied in a wide variety of forms, some of which may be quite different from those in the disclosed embodiment. Consequently, the specific ingredients and functional details disclosed herein are merely representative, yet in that regard, they are deemed to afford the best embodiment for purposes of disclosure and to provide a basis for the claims herein which define the scope of the present invention.

Moreover, well known methods and procedures for both carrying out the objectives of the present invention and illustrating the preferred embodiment are incorporated herein by reference but have not been described in detail as not to unnecessarily obscure aspects of the present invention.

The present invention relates to personal microdermabrasion soap compositions containing high amounts of uniformly dispersed, large abrasive particles and methods of making same. The present invention may be made and used as a soap bar. In one method, the soap bar of the invention is moistened with water and rubbed gently on wet human skin. The abrasives that are embedded in the soap and/or contained in the lather will exfoliate the desired area of the skin. Alternatively, a suitable amount of the soap composition can be applied to the skin via intermediate application to a washcloth, a sponge, or other washing device. The soap composition of the invention can be removed by rinsing the composition with copious amounts of water.

The microdermabrasion soap bar of the preferred embodiment helps to improve skin texture, clarity, and the appearance of uneven skin tone. The soap also aids in relieving itchy and dry skin, and has been shown to be an effective home treatment for Keratosis Pilaris, folliculitis, and an effective adjunct to cellulite treatments.

The microdermabrasion of the present invention preferably appears light-colored for a pleasing visual effect. Specifically, the lightness of the color of the soap lies between 5 and 10 on the Munsell value scale as defined by the Munsell Color System.

The microdermabrasion soap bar as defined by the present invention is efficacious for cleansing the skin while minimizing the irritation or scarring that are commonly associated with large sized abrasives. The objectives are achieved by uniformly dispersing approximately 8% to approximately 15% by weight of abrasives, preferably magnesium oxide, having a mean particle size diameter from approximately 120 to approximately 200 microns, within a bar soap by utilizing approximately 0.5% to approximately 3.5% by weight of dispersing agents. The dispersing agents of the present invention comprise both an oil component and a butter component, both of which are preferably derived from different plant sources. The dispersing agents may also comprise approximately 0.1% to approximately 1.5% by weight of essential oils for possible additional benefits such as fragrant and antibacterial properties. Preferably, the total weight percent of oils, butters and essential oils should not be used in high amounts in order to maintain a sufficient foamability of the soap of the present invention. Importantly, the incorporation of high amounts of large abrasives by the utilization of the dispersing agents, comprising both an oil component and a butter component, maintains the integrity of the soap bar. Furthermore, the incorporation of the dispersing agents in the soap compositions of the present invention does not affect the apparent volume of foam generated by the soap of the present invention compared to a common soap.

The abrasives used in the invention must be sufficiently spread apart throughout the entire volume of the soap. This prevents any one area of the soap from bearing significantly more abrasives that are visually and tactilely detectable than other areas of the soap. It is this uniform dispersion of large abrasives that makes the soap an effective soap. Thus, the soap of the invention provides extra abrading power without unnecessary irritation or scarring of the skin.

Preferably, a mean particle diameter size of abrasives is from approximately 120 to approximately 200 microns, and more preferably approximately 150 microns. The abrasive particles are utilized in high amounts to provide strong abrading effects and tactile perception that the skin is being exfoliated. Preferably, the total amount of the abrasives that are used in the soap bar compositions of the present invention is from approximately 8% to approximately 15%.

In a preferred embodiment, the abrasive comprises magnesium oxide (MgO). Magnesium oxide abrasives help to keep the light, aesthetically pleasing color of the soap. In contrast, many commonly used abrasives, such as corundum or pumice significantly darken the color of the soap. Preferably, the lightness of the color of the soap of the present invention lies between 5 and 10 on the Munsell value scale as defined by the Munsell Color System. Magnesium oxide crystals are also soft relative to harder crystals such as aluminum oxide. Thus, magnesium oxide abrasives provide a gentler, yet effective abrading effect.

In one embodiment, the abrasive is a blend comprising approximately 98% to approximately 100% by weight of magnesium oxide, approximately 0.65% by weight of calcium oxide, approximately 0.06% by weight of aluminum oxide ($Al_2O_3$), approximately 0.06% by weight of silica ($SiO_2$), and approximately 0.05% by weight of iron (III) oxide ($Fe_2O_3$). Preferably, the abrasives comprising the blend have a mean particle diameter size of approximately 150 microns and particle size distribution from approximately 90 to approximately 220 microns. The blend of abrasives used in a preferred embodiment is available from Brenntag Specialties, Inc. under the trade name "Dermag 140". The preferred amount of the blend in the soap bar composition ranges approximately 8% to approximately 15% by weight. Most preferably, approximately 10% by weight of the blend is utilized in the present invention. The uniform distribution of abrasives provides the skin with effective dermabrading properties without the ripping of skin pores and/or bleeding of the skin.

Furthermore, the soap of the present invention may utilize a plurality of abrasive particles known in the art. Abrasives that are suitable for use in the microdermabrasion soap bar of the present invention include natural, synthetic origin, or a mixture of both. Such abrasive materials include, but are not limited to those selected from the group consisting of magnesium oxide, iron oxide, aluminum oxide, boron oxide, calcium oxide, attapulgite, aluminum silicate, bismuth oxychloride, boron nitride, calcium carbonate, calcium phosphate, calcium pyrophosphate, calcium sulfate, silica, sodium bicarbonate, almond meal, apricot seed powder, algae, barley flour, argan nut powder, cellulose, chalk, chitin, clay, corn flour, jojoba seed powder, pecan shell powder, loofah, oatmeal, diamonds, garnets, sapphires, rubies, emeralds, topaz, and other similar materials precious stones or the like.

The soap bar composition of the present invention further comprises dispersing agents. The dispersing agents are essential for the uniform suspension of abrasives within a soap bar without significantly compromising the integrity and foamability of the soap bar. The composition of the present invention comprises from approximately 0.5% to approximately 3.5% by weight of dispersing agents. The dispersing agents comprise both a butter component and an oil component, with both such oil and butter components having about C8-24 saturated or unsaturated aliphatic chains. More specifically, the soap of the present invention comprises from approximately 0.2% to approximately 0.5% by weight of an oil component and from approximately 0.3% to approximately 1.1% by weight of a butter component. The correct proportions of the oil and butter components not only keep the soap billet intact during its manufacturing process, but also maintain the foamability of the soap. In a preferred embodiment, the dispersing agents may further comprise essential oils. Preferably, the dispersing agents comprise lipid materials derived from plants such as oils and butters. Generally, oils are liquid and butters are solid or semi-solid at room temperature (25° C.). Both oils and butters comprise triglycerides, diglycerides, monoglycerides and free fatty acids. Their relative amounts vary depending on the type of lipid material.

Vegetable oils are preferably used in the oil component of the dispersing agents. Vegetable oils have proven their effectiveness in cosmetics and toiletries, and many have been effectively used to alleviate skin disorders such as eczema, psoriasis and acne. The vegetable oil used in the invention can be extracted from their source by chemical or physical extraction known in the art followed by purification steps. For example, one such chemical extraction utilizes carbon dioxide or solvent such as hexane, while one such physical extraction is achieved by expeller-press, screw press, or ram press method. Sources of vegetable oils are generally plant seeds or nuts, but plant extracts dissolved in a vegetable oil may also be useful for the soap bar composition of the present invention. One such example is aloe vera oil, which typically comprises soybean oil and aloe extract. Preferably, the soap composition of the present invention comprises from approximately 0.2% to approximately 0.5% by weight of an oil component comprising olive oil.

Some examples of vegetable oils suitable for uniformly dispersing the abrasives include, but are not limited to *Cocos nucifera* (coconut) oil, *Olea europaea* (olive) oil, *Elaeis guineensis* (palm) oil, palm kernel oil, *Helianthus annuus* (sunflower) seed oil, safflower oil, corn oil, *Macadamia ternifolia* (macadamia) seed oil, *Coffea arabica* (green coffee) oil, *Aleurites moluccana* (kukui) nut oil, *Simmondsia chinensis* (jojoba) seed oil, *Prunus amygdalus dulcis* (sweet almond) oil, *Persea gratissima* (avocado) oil, *Ricinus communis* (castor) seed oil, Sulfated *Ricinus communis* (castor) oil, *Argania spinosa* (argan) nut oil, *Euterpe oleracea* fruit (acai berry) oil, *Carapa guianensis* (andiroba) nut oil, *Prunus armeniaca* (apricot) kernel oil, *Glycine soja* (soybean) oil, *Adansonia digitata* (baobab) seed oil, *Rubus Occidentalis* (black raspberry) seed oil, *Rubus Fruticosus* (blackberry) seed oil, *Ribes nigrum* (blackcurrant) fruit oil, *Vaccinium corymbosum* (blueberry) seed oil, *Borago officinalis* (borage) seed oil, *Brassica oleracea italica* (broccoli) seed oil, *Sclerocarya birrea* (marula) kernel oil, cucumber seed Oil, *Ricinodendron rautanenii* (manketti) oil, *Passiflora incanata* (passion flower) seed oil, *Camelina sativa* (camelina) seed oil, *Linum usitatissimum* (linseed) oil, *Fragaria annassa* (strawberry) seed oil, *Oleum Papaveris* (poppy) seed oil, *Moringa oleifera* (moringa) oil, *Oryza sativa* (rice) bran oil, *Punica granatum linn* (pomegranate) oil, *Cucurbita pepo* (pumpkin) seed oil, *Juglans regia* (walnut) seed oil, *Algooquian pacaan* (pecan) nut oil, and any combination thereof.

Preferably, the dispersing agents also comprise a butter component. The butter component most preferably comprises vegetable butters. Vegetable butters can be created by blending plant extracts with fatty fractions of the same or different plant. One such example is aloe butter, which comprises aloe extract and cocoa butter. Vegetable butters can also be obtained by blending the fatty fractions of a vegetable oil. Fatty fractions can be combined with other fatty fractions from the same or different plant source. An example of fatty fraction is an unsaponifiable fraction containing paraffin, tocopherols and sterols. The percentage of the unsaponifiable fraction of a vegetable oil is usually very low and thus, unsaponifiable fractions are sometimes blended with refined vegetable oils that have undergone hydrogenation. Generally, it requires a large quantity of processed oil to yield a significant quantity of butter. Vegetable butters generally have a high content of symmetrical triglyceride comprising saturated and monounsaturated fatty acids, in particular stearic acid and oleic acid.

Vegetable butters are becoming more widely incorporated into cosmetics and skin care products for their rich moisturizing properties. Furthermore, certain butters such as cocoa butter and sal butter contribute to the viscosity and stability of emulsions, and give rigidity to products such as lotion bars and balms. Thus, an adequate amount of butters are indispensible for the soap bar composition of the present invention, although too much butter may compromise the foamability of the soap. Preferably, the soap composition of the present invention comprises from approximately 0.3% to approximately 1.1% by weight of a butter component comprising shea butter and aloe butter.

Some examples of butters suitable for uniformly dispersing the abrasives include, but are not limited to *Mangifera indica* (mango) seed butter, aloe butter, *Olea europa* (olive) butter, *Coffea arabica* (coffee) bean butter, macadamia nut butter, *Persea Gratissima* (avocado) butter, *Theobroma cacao* (cocoa) seed butter, hemp seed butter, *Shorea stenoptera* (illipe) seed butter, *Garcinia indica* (kokum) seed butter, pistachio nut butter, *Butyrospermum parkii* (shea butter), *Prunus amygdalus dulcis* (sweet almond) butter, grape seed butter, *Bassia latifolia* (mowrah) butter, *Prunus armeniaca* (apricot) butter, *Shorea robusta* (sal) butter, *Glycine soja* (soy) butter, *Triticum vulgare* (wheat germ) butter, and any combination thereof.

The dispersing agents may also comprise an essential oil. Essential oils, sometimes called aromatic plant essences, can be utilized in addition to the oil and butter components to help suspend the abrasives uniformly within the soap bar. Essential oils are fragrant volatile liquids that are generally extracted by distillation or solvent extraction. Due to their hydrophobic nature, they are insoluble in water but solvate rapidly in fixed vegetable oil, alcohol and ether. Essential oils also add many other beneficial properties to the resulting soap bar. Some of such properties include pleasant aroma, antiseptic, or analgesic properties.

Plant sources from which useful essential oils for the present invention can be extracted include, but are not limited to *Citrus aurantium* L. ssp. *Bergamia, Citrus aruantium* L. ssp. *Amara, Betula lenta, Melaleuca cajuputi, Daucus carota* L., *Cedrus atlantica, Matricaria chamomilla* L., *Anthemis nobilis* L., *Cinnamomum zeylanicum, Cymbopogon nardus* L., *Eugenia caryophyllus, Citrus limonum* L., *Cymbopogon flexuosus, Origanum majorana* L., *Melissa officinalis* L., *Citrus aurantium* L., *Melaleuca viridiflora quinquenervia, Myristica fragrans, Citrus sinensis* L., *Origanum heracleoticum* L., *Coriandrum sativum* L., *Cymbopogon martini, Cuminum cyminum* L., *Cupressus sempervirens* L., *Mentha piperita* L., *Santalum austrocaledonicum, Zingiber officinale, Pogostemon cablin, Picea mariana, Boswellia carteri, Melaleuca alternifolia, Pinus sylvestris* L., *Lavandula hybrid, Lavandula angustifolia, Citrus paradisii, Eucalyptus citriodora, Gaultheria fragrantissima, Juniperus communis* L., *Aniba rosaeodora, Eucalyptus radiate, Eucalyptus globules, Rosmarinus officianlis* L., *Pimento officinalis , Nepeta cataria, Salvia sclarea, Anethum graveolens, Juniperus communis* and any combination thereof.

The composition of the invention may utilize a fragrance composition comprising a blend of essential oils and synthetic aroma compounds. The blend is often diluted with a carrier like propylene glycol, vegetable oil, or mineral oil. Some examples of synthetic aroma compound that are suitable for soap bar compositions of the present invention include, but are not limited to benzaldehyde, citral, vanillin, ethyl acetate, fructone, octyl acetate, pentyl butanoate, pentyl pentanoate, methyl salicylate, isoamyl acetate, limonene, citronellol, and mixtures thereof. Preferably, the fragrance containing the essential oil is present in the composition of the invention in an amount between approximately 0.1% to approximately 1.5% by weight.

Oils, butters, and essential oils can be combined in any way so as to achieve the desired aroma, foamability, integrity, moisturizing ability, and any additional properties. Importantly, essential oils and the oil and butter components can be used in the bar soap without significantly affecting the foamability and integrity of the soap. As an illustrative example, the dispersing agents comprise olive oil, shea butter, aloe butter, and lemongrass fragrance oil in order to provide refreshing aroma, uniform dispersion of abrasives, integrity of the soap, and sustained foamability.

The invention further includes ingredients that are commonly used in soap bar compositions. Some examples of such ingredients include, but are not limited to surfactants, chelating agents, antioxidants, opacifying agents and colorants.

The composition of the present invention may comprise one or more surfactants selected from a group consisting of anionic surfactants, cationic surfactants, amphoteric surfactants, nonionic surfactants, zwitterionic surfactants and any combinations thereof. As it is well known in the art that surfactant materials can also be an emulsifier, the term "surfactant" does not exclude materials which also have emulsification properties. The surfactants that are used in the soap bar compositions of the present invention may be present in an amount from approximately 60% to approximately 90%, preferably from approximately 70% to approximately 85% by weight. Preferably, the soap composition of the present invention may comprise alkali metal salts of fatty acids such as sodium palmitate and sodium oleate (i.e. anionic surfactants). Among the anionic surfactants that are used herein may be saponified glycerides from plant or animal sources such as sodium palmate, sodium palm kernelate, sodium cocoate, sodium tallowate, potassium tallowate, and sodium lardate.

In a preferred embodiment, anionic surfactants derived from plant-derived glycerides, more preferably from at least two different sources are used (e.g. palm oil and coconut oil). Such glycerides usually contain about 8 to 24 aliphatic carbon atoms. Some examples of vegetable oils from which anionic surfactants are derived include, but are not limited to palm oil, palm kernel oil, olive oil, coconut oil, soybean oil, almond oil, jojoba oil, and avocado oil. Other anionic surfactants may also be used in place of or in conjunction with plant-derived or animal-derived anionic surfactants. Some examples of such anionic surfactants include but are not limited to sodium laureth-6 carboxylate, sodium lauramido diacetate, sodium trideceth-7 carboxylate, sodium stearoyl lactalbumin, and mixtures thereof. Sulfur-containing anionic surfactants, such as alkoyl isethionates including ammonium cocoyl isethionate, sodium cocoyl isethionate, sodium lauroyl isethionate, sodium tridecylbenzenesulfonate and mixtures thereof may also be used. Alternatively, synthetically prepared fatty acids (e.g. by oxidation of petroleum stocks or by the Fischer-Tropsch process) may be used alone or in combination with the fatty acid salts of natural origin.

Cationic surfactants may be used in the present invention to add or enhance certain properties. For example, certain long alkyl chain quaternary ammonium compounds such as cetyl trimethyl ammonium chloride function as a surfactant and an antimicrobial agent. Amine oxides such as N-tetracosyl dimethyl amine oxide may have good foaming properties and are nonirritating to the skin. Some other non-limiting examples of cationic surfactants that may be useful herein include, but are not limited to amninoamides (e.g. stearamidopropyl PG-dimonium chloride phosphate, stearamidopropyl dimethyl ammonium lactate, stearamidopropyl dimethyl ammonium chloride) and quaternary ammonium salts (e.g. cetyl ammonium chloride, dimethyl ammonium chloride, stearyl ammonium chloride, cetyl dimethyl ammonium bromide, lauryl dimethyl ammonium bromide, ditallow dimethyl ammonium chloride, di(coconutalkyl)dimethyl ammonium chloride, di(coconutalkyl)dimethyl ammonium bromide).

Some examples of nonionic surfactants that may be useful herein include, but are not limited to condensation products of long chain alcohols with sugar or starch polymers (e.g. decyl polyglucoside and lauryl polyglucoside), amides (e.g. cocoamide diethanolamine and cocoamide monoethanolamine), alkylene oxide derived surfactants (e.g. ceteth-6, ceteareth6, steareth-6, PEG-12 stearate, and PEG-200 glyceryl tallowate) and mixtures thereof.

Some examples of zwitterionic or amphoteric surfactants that may be useful herein include, but are not limited to betaine surfactants (e.g. coco dimethyl carboxymethyl betaine, lauryl dimethyl carboxymethyl betaine, and stearyl bis-(2-hydroxypropyl) carboxymethyl betaine, and sodium lauryl diethylene diamnioglycinate), sultaines (e.g. cocamidopropyl hydroxysultaine and sodium lauroyl sarcosinate), and mixtures thereof.

The composition of the invention may also comprise one or more chelating agents and/or antioxidants. Compositions containing high proportions of unsaturated fatty acids (e.g. oleic, linoleic, or linolenic acids) and certain soap additives, such as fragrance, tend to be susceptible to undesirable atmospheric oxidative changes. Therefore, chelating agents and antioxidants are necessary to prevent such oxidation from occurring. In addition, certain chelating agents such as ethylenediaminetetraacetate (EDTA) are also capable of scavenging ions and microbes in the soap. Some nonlimiting example of chelating agents that are useful for the instant invention include but are not limited to disodium EDTA, trisodium EDTA, tetrasodium EDTA, diammonium EDTA, tripotassium EDTA, calcium disodium EDTA, TEA-EDTA, tetrasodium etidronate, pentasodium pentetate, sodium gluconate, trisodium citrate, disodium citrate. Some examples of antioxidants include, but are not limited to citric acid, magnesium silicate, butylatehydroxytoluene (BHT), tetradibutyl hydroxyhydrocinnamate and mixtures thereof.

The composition of the invention may also include one or more opacifying agents and/or colorants (i.e. food and/or cosmetic grade dyes) that alter the appearance of the soap. Some examples of opacifying agents include, but are not limited to titanium dioxide, zinc oxide, aluminum hydroxide, and mixtures thereof. Some examples of food and/or cosmetic grade dyes include, but are not limited to Acid Blue 9 Aluminum Lake, Acid Red 33, Acid Yellow 23 Aluminum Lake, Aka 106, Blue 1 Lake, Brown 1, Acid Black 1, C175170, Gold, Green 3, Henna, Ki4, Lactoflavin, Mica, Murasaki401, Midori401, Orange4, Pigment Green 7, Pigment Red 5, Pigment Yellow 73, any of the Red Lakes, and mixtures thereof.

The composition of the invention may also include carriers such as water and glycerol. The permissible water content in the composition of the present invention includes up to approximately 15%, and preferably up to approximately 10% by weight. This is necessitated by the high loading of the abrasives, as minimum liquid content is necessary to allow the uniform dispersion and dense packing of the abrasives. Otherwise, the soap may crumble or form concentrated areas of abrasives. Glycerol, also called glycerin or glycerine, is preferably present in the soap composition of the present invention in an amount between approximately 1% and approximately 15%, more preferably between approximately 3% and approximately 9% by weight. Glycerol complements the moisturizing and abrasive-suspending properties of the dispersing agents.

Other additives can be made a part of the soap bar composition in order to introduce additional properties to or enhance the existing properties of the soap. Such additives may include but are not limited to vitamins (e.g. vitamins A, C, and E), humectants other than glycerin (e.g. diglycerin, propylene glycol, glyceryl triacetate,. and sorbitol), anti-bacterial agents (e.g. triclocarban or triclosan), and anti-acne agents (e.g. salicylic acid or benzoyl peroxide).

As an illustrative example, bars of the present invention may be made by mixing appropriately weighed out ingredients in a blender or other mixing means. After the mixture is refined at least twice, the mixture is then extruded into a nose cone and against an extrusion plate which causes soap mixture to solidify. The soap billet can then be placed into a soap die and pressed into a desirable shape. The soap bars of the present invention may be of varying sizes and shapes such as ovoid, sphere, rectangle, etc. with flat or curved profile. The soap bars may also have smooth or textured surface.

The following examples further describe and demonstrate embodiments within the scope of the invention. The examples are given solely for the purpose of illustration and are not to be construed as limitations of the present invention, as many variations are possible without departing from the spirit and scope of the invention.

EXAMPLE 1

| Ingredients | Concentration range (% w/w) |
|---|---|
| Sodium Palmate | 40-70 |
| Sodium Cocoate | 20-65 |
| Water | up to 15 |
| Magnesium oxide | 8-15 |
| Aluminum oxide | 0.01-0.03 |
| Glycerin | 3-9 |
| Fragrance | 0.5-1.5 |
| Shea Butter | 0.2-0.7 |
| Aloe Butter | 0.1-0.4 |
| Olive Oil | 0.2-0.5 |
| Titanium Dioxide | 0.1-0.3 |
| Pentasodium pentetate | up to 0.01 |
| Tetrasodium Etidronate | up to 0.01 |
| Disodium EDTA | 0.1-0.2 |

EXAMPLE 2

| Ingredients | Weight Percent |
|---|---|
| Sodium Palmate | 50 |
| Sodium Cocoate | 25 |
| Water | 9.95 |
| Magnesium oxide | 10 |
| Aluminum oxide | 0.01 |
| Glycerin | 3.7 |
| Fragrance | 0.5 |
| Shea Butter | 0.2 |
| Aloe Butter | 0.12 |
| Olive Oil | 0.2 |
| Titanium Dioxide | 0.3 |
| Pentasodium pentetate | 0.01 |
| Tetrasodium Etidronate | 0.01 |
| Total | 100 |

While the present invention has been described with reference to the preferred embodiment and alternative embodiments, which have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A personal cleansing composition for a microdermabrasion soap bar comprising:
   (a) from approximately 8% to approximately 15% by weight of an abrasive blend having a mean particle size diameter of approximately 120 microns to approximately 200 microns,
   wherein said abrasive blend comprises, based on the total weight of said abrasive blend, approximately 98% by weight of magnesium oxide, approximatly 0.05% by weight of iron oxide, approximately 0.06% by weight of aluminum oxide, approximately 0.65% by weight of calcium oxide, and approximately 0.06% by weight of silca;
   (b) dispersing agents comprising an oil component and a shea and aloe butter component; and
   (c) from approximately 10% to approximately 15% by weight of a carrier;
   wherein said abrasive is dispersed uniformly within said microdermabrasion soap.

2. A composition according to claim 1, wherein said microdermabrasion soap bar has a color with a lightness that lies between 5 and 10 on the Munsell value scale as defined by the Munsell Color System.

3. A composition according to claim 1, wherein an apparent volume of foam generated by said microdermabrasion soap bar is essentially the same as an apparent volume of foam generated by a soap bar comprising no abrasive.

4. A composition according to claim 1, wherein said oil is present in an amount between approximately 0.2% and approximately 0.5% by weight.

5. A composition according to claim 1, wherein said butter is present in an amount between approximately 0.3 and approximately 1.1% by weight.

6. A composition according to claim 1, further comprising a humectant selected from the group consisting of glycerin, diglycerin, propylene glycol, glyceryl triacetate, sorbitol, and combinations thereof.

7. A composition according to claim 6, wherein said humectant is present in an amount between approximately 1% and approximately 15% by weight.

8. A composition according to claim 1, further comprising a surfactant.

9. A composition according to claim 4, wherein said surfactant is an anionic surfactant derived from a vegetable oil selected from the group consisting of palm oil, palm kernel oil, olive oil, coconut oil, soybean oil, almond oil, jojoba oil, and avocado oil, corn oil, castor oil, rice bran oil, and combinations thereof.

10. A composition according to claim 9, further comprising a surfactant selected from the group consisting of cationic surfactant, nonionic surfactant, zwitterionic surfactant, amphoteric surfactant, and combinations thereof.

11. A composition according to claim 8, wherein said surfactant is a cationic surfactant selected from the group consisting of cetyl trimethyl ammonium chloride, N-tetracosyl dimethyl amine oxide, stearamidopropyl PG-dimonium chloride phosphate, stearamidopropyl dimethyl ammonium lactate, stearamidopropyl dimethyl ammonium chloride, cetyl ammonium chloride, dimethyl ammonium chloride, stearyl ammonium chloride, cetyl dimethyl ammonium bromide, lauryl dimethyl ammonium bromide, ditallow dimethyl ammonium chloride, di(coconutalkyl)dimethyl ammonium chloride, di(coconutalkyl)dimethyl ammonium bromide, decyl polyglucoside, lauryl polyglucoside, cocoamide diethanolamine, cocoamide monoethanolamine, ceteth-6, ceteareth6, steareth-6, PEG-12 stearate, PEG-200 glyceryl tallowate, coco dimethyl carboxymethyl betaine, lauryl dimethyl carboxymethyl betaine, stearyl bis-(2-hydroxypropyl) carboxymethyl betaine, sodium lauryl diethylene diamnioglycinate), cocamidopropyl hydroxysultaine, sodium lauroyl sarcosinate, and combinations thereof.

12. A composition according to claim 1, wherein the total amount of said oil and said butter is between approximately 0.5% and approximately 3.5% by weight.

13. A composition according to claim 1, further comprising a fragrance including an essential oil.

14. A composition according to claim 10, wherein the total amount of said oil, said butter, and said fragrance is between approximately 0.5% and approximately 3.5% by weight.

15. A composition according to claim 1, wherein said oil component and said butter component are derived from a plant source.

16. A composition according to claim 1, wherein said oil component is selected from the group consisting of coconut oil, olive oil, palm oil, palm kernel oil, canola oil, sunflower seed oil, safflower oil, macadamia seed oil, green coffee oil, kukui nut oil, jojoba oil, sweet almond oil, avocado oil, castor seed oil, castor oil, argan nut oil, acai berry oil, andiroba nut oil, apricot kernel oil, soybean oil, baobab seed oil, black raspberry seed oil, blackberry seed oil, blackcurrant fruit oil, blueberry seed oil, borage seed oil, broccoli seed oil, marula kernel oil, cucumber seed Oil, manketti oil, passion flower seed oil, camelina seed oil, linseed seed oil, strawberry seed oil, poppy seed oil, moringa oil, rice bran oil, pomegranate oil, pumpkin seed oil, walnut seed oil, pecan nut oil, and combinations thereof.

17. A composition according to claim 1, wherein said butter component is at least one of mango butter, aloe butter, olive butter, coffee bean butter, macadamia nut butter, avocado butter, cocoa butter, hemp butter, illipe butter, kokum butter, pistachio nut butter, shea butter, sweet almond butter, grape seed butter, mowrah butter, apricot butter, sal butter, soy butter, wheat germ butter, and combinations thereof.

18. A personal cleansing composition for a light-colored microdermabrasion soap bar comprising:
   (a) from approximately 8% to approximately 15% by weight of an abrasive blend comprising magnesium oxide having a mean particle size diameter of approximately 150 microns,
   wherein said abrasive blend comprises, based on the total weight of said abrasive blend, approximately 98% of said magnesium oxide, and said abrasive blend further comprises, based on the total weight of said abrasive blend, approximately 0.05% by weight of iron oxide, approximately 0.06% by weight of aluminum oxide, approximately 0.65% by weight of calcium oxide, and approximately 0.06% by weight of silica;
   (b) from approximately 0.2% to approximately 0.5% by weight of an oil component selected from the group consisting of olive oil, rice bran oil, castor oil, canola oil, avocado oil, sweet almond oil, coconut oil, palm oil, palm kernel oil, corn oil, cottonseed oil, grapeseed oil, jojoba oil, hemp seed oil, safflower oil, soybean oil, wheat germ oil, or combinations thereof;
   (c) from approximately 0.3% to approximately 1.1% by weight of a butter component selected from at least one of shea butter, aloe butter, mango butter, olive butter, coffee butter, avocado butter, soy butter, and combinations thereof; and
   (d) from approximately 60% to approximately 90% by weight of surfactants;
   wherein said abrasives are uniformly dispersed within said microdermabrasion soap bar.

19. A method of uniformly distributing an abrasive blend having a mean particle size diameter of approximately 120 microns to approximately 200 microns into a soap bar comprising:
   (a) providing from approximately 5 to approximately 15% of said abrasive blend by weight,
   wherein said abrasive blend comprises, based on the total weight of said abrasive blend, approximately 98% by weight of magnesium oxide, approximately 0.05% b weight if iron
   (b) providing from approximately 0.5% to approximately 3.5% by weight of dispersing agents comprising an oil component and a shea and aloe butter component;
   (c) forming a homogeneous soap bar composition by mixing said abrasive blend and said dispersing agent; and
   (d) solidifying said soap bar composition by extruding said composition onto an extrusion plate;
   wherein said dispersing agents uniformly disperse said abrasive blend within said soap bar composition.

20. A personal cleansing composition for a microdermabrasion soap bar comprising:
   (a) from approximately 8% to approximately 15% by weight of an abrasive blend having a mean particle size diameter of approximately 120 microns to approximately 200 microns,
   wherein said abrasive blend comprises iron oxide, aluminum oxide, calcium oxide, silica, and approximately 98% by weight of magnesium oxide based on the total weight of said abrasive blend;
   (b) dispersing agents comprising an oil component and a butter component; and
   (c) from approximately 10% to approximately 15% by weight of a carrier;
   wherein said abrasive is dispersed uniformly within said microdermabrasion soap.

21. A personal cleansing composition for a microdermabrasion soap bar comprising:
   (a) from approximately 8% to approximately 15% by weight of an abrasive blend having a mean particle size diameter of approximately 150 microns,
   wherein said abrasive blend comprises iron oxide, aluminum oxide, calcium oxide, silica, and approximately 98% by weight of magnesium oxide based on the total weight of said abrasive blend;
   (b) from approximately 0.2% to approximately 0.5% by weight of an oil component selected from at least one of olive oil, rice bran oil, castor oil, canola oil, avocado oil, sweet almond oil, coconut oil, palm oil, palm kernel oil, corn oil, cottonseed oil, grapeseed oil, jojoba oil, hemp seed oil, safflower oil, soybean oil, wheat germ oil, or combinations thereof;
   (c) from approximately 0.3% to approximately 1.1% by weight of a butter component selected from at least one of shea butter, aloe butter, mango butter, olive butter, coffee butter, avocado butter, soy butter, or combinations thereof; and
   (d) from approximately 60% to approximately 90% by weight of surfactants;
   wherein said abrasives are uniformly dispersed within said microdermabrasion soap bar.

22. A personal cleansing composition for a microdermabrasion soap bar comprising:
   (a) from approximately 8% to approximately 15% by weight of an abrasive blend having a mean particle size diameter of approximately 150 microns,
   wherein said abrasive blend comprises iron oxide, aluminum oxide, calcium oxide, silica, and approximately 98% by weight of magnesium oxide based on the total weight of said abrasive blend;
   (b) from approximately 0.2% to approximately 0.5% by weight of an oil component;
   (c) from approximately 0.3% to approximately 1.1% by weight of a butter component;
   (d) from approximately 60% to approximately 90% by weight of surfactants; and
   (e) from approximately 10% to approximately 15% by weight of a carrier;
   wherein said abrasives are uniformly dispersed within said microdermabrasion soap bar, and wherein said microdermabrasion soap bar has a color with a lightness that lies between 5 and 10 on the Munsell value scale as defined by the Munsell Color System.

* * * * *